US007122357B2

(12) United States Patent
Sander-Struckmeier et al.

(10) Patent No.: US 7,122,357 B2
(45) Date of Patent: Oct. 17, 2006

(54) METHOD FOR THE TREATMENT OF DIABETES

(75) Inventors: Suntje Sander-Struckmeier, Hannover (DE); Claus Rudolf Steinborn, Seelze (DE); Martin A. Rudmann, Wathlingen (DE); Diethard Schwanitz, Eime (DE); Friederike Henniges, Braunschweig (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 483 days.

(21) Appl. No.: 09/953,450

(22) Filed: Sep. 17, 2001

(65) Prior Publication Data

US 2002/0061302 A1    May 23, 2002

Related U.S. Application Data

(63) Continuation of application No. PCT/EP00/02261, filed on Mar. 15, 2000.

(30) Foreign Application Priority Data

Mar. 17, 1999    (DE) ................................ 199 11 778

(51) Int. Cl.
*C12N 9/00*    (2006.01)
(52) U.S. Cl. .................................... 435/183
(58) Field of Classification Search ............... 435/186, 435/198, 201, 219; 514/866; 424/94.21, 424/94.6, 94.63
See application file for complete search history.

(56) References Cited

U.S. PATENT DOCUMENTS 3,803,305 A    4/1974    Thuillier

FOREIGN PATENT DOCUMENTS

DE    2512746    4/1977
DE    4203315    8/1992
SU    908352    *    2/1982

OTHER PUBLICATIONS

Nakamura et al., Pancreas, vol. 16, No. 3, 329-36.*
Fallis et al., Annals of Surgery, Oct. 1948, pp. 639-667.*
Murlin et al., Proceedings of the Society for Experimental Biology and Medicine, vol. 14, pp. 8-9, 1917.*
M. Delhaye, "Comparative Evaluation of a High Lipase Pancreatic Enzyme Preparation and a Standard Pancreatic Supplement for Treating Exocrine Pancreatic Insufficiency in Chronic Pancreatitis" European Journal of Gastronenterology and Hepatology, 1996.
I. Simek, "Substitution Therapy in Insufficient External Pancreatic Secretion" Online Medline Database, 1993.
D. D'Costa, "Diabetic Neuropathic Cachexia Associated with Malabsorption" Diabetic Medicine, 1992.
Copy of the International Search Report.
H. P. Klotz, Lyophilized Pancreatic Extract, an Aid in the Treatment of Mild Diabetes, La Nouvelle Presse medicals, Oct. 1975 (in French and English, abstract.
Goodman and Gilman's "The Pharmacological Basis of Therapeutics", 8th ed. Pergamon Press 1990: p. 1471-1477.
Printout of the online "Diabetes Dictionary" of the American Diabetes Association®.

* cited by examiner

*Primary Examiner*—Michael Meller
(74) *Attorney, Agent, or Firm*—Crowell & Moring LLP

(57) ABSTRACT

The use of physiologically acceptable enzyme mixtures having lipolytic, proteolytica and amylolytic activity, of microbial or animal origin, preferably digestive enzyme mixtures such as pancreatin or digestive enzyme mixtures containing pancreatin, for the treatment of diabetes. The invention also relates to the production of pharmaceutical compositions suitable for such treatment. A preferred variant of the invention relates to use of this enzyme mixture having lipolytic, proteolytic and amylolytic activity, especially digestive enzyme mixtures such as pancreatin or digestive enzyme mixtures containing pancreatin, for the adjuvant treatment of type I or type II diabetes mellitus.

7 Claims, No Drawings

METHOD FOR THE TREATMENT OF DIABETES

CROSS REFERENCE TO RELATED APPLICATIONS

This application is a continuation of International Patent Application No. PCT/EP00/02261, filed Mar. 15, 2000 designating the United States of America, the entire disclosure of which is incorporated herein by reference. Priority is claimed based on Federal Republic of Germany patent application No. DE 199 11 778.0, filed Mar. 17, 1999.

BACKGROUND OF THE INVENTION

The present invention relates to the use of physiologically acceptable enzyme mixtures with lipolytic, proteolytic and amylolytic activity, but especially of mixtures of digestive enzymes such as pancreatin, for the treatment of diabetes and for the manufacture of medicinal products suitable for this treatment. The invention relates especially to the use of these enzyme mixtures with lipolytic, proteolytic and amylolytic activity, but especially of pancreatin or mixtures of digestive enzymes containing pancreatin, for the adjuvant therapy of both type I and type II primary diabetes.

As used herein the term "diabetes" is understood to mean diabetes mellitus, the so-called "sugar sickness". In addition to other, e. g. secondary forms of diabetes that can occur as sequelae of other primary diseases, two main groups of disorders of carbohydrate metabolism are distinguished, i. e. type I diabetes due to insulin deficiency and type II diabetes due to reduced insulin effectiveness, the course of the disease depending on the type concerned, among other factors. Diabetes is furthermore a chronic disease with a variety of pathological manifestations and is accompanied, for example, by disorders of lipid metabolism, circulation and glucose metabolism. The typical symptoms of this disease include elevated blood sugar (hyperglycemia), excretion of sugar in the urine (glycosuria), tendency to infections and pruritus. Diabetes tends to be a progressive disorder and in many cases is also accompanied by various complications. Known complications include, for example, neurologic and vascular diseases. It is therefore necessary to adjust the therapy to meet each patient's individual requirements in every phase of the illness and to select the suitable medicinal product for each individual case. It may also be desirable for this therapy to supplement the selected primary medications with other medicinal products in the form of an adjuvant treatment which can exert a supporting effect on the therapy and beneficially influence the further course of the illness.

SUMMARY OF THE INVENTION

Therefore, it is an object of the invention to provide a new method for the treatment of diabetes mellitus.

It is another object of the invention to provide new pharmaceutical preparations for the treatment of diabetes mellitus.

It is a particular object of the invention to provide new pharmaceutical preparations for adjuvant therapy in the treatment of diabetes which exert an additional supportive effect on the treatment and beneficially influence the further course of the diabetic illness, for example by reducing the incidence of late complications.

According to the invention, physiologically acceptable enzyme mixtures with lipolytic, proteolytic and amylolytic activity, such as suitable enzyme mixtures of microbial origin and/or especially mixtures of digestive enzymes of animal origin such as preferably pancreatin or pancreatin-like mixtures of digestive enzymes, are used for the treatment of diabetes mellitus in larger mammals and humans, and for the manufacture of pharmaceutical preparations for such treatment.

For the present invention, physiologically acceptable enzyme mixtures with lipolytic, proteolytic and amylolytic activity can be used that are of any animal or microbiological origin. The enzyme mixtures with lipolytic, proteolytic and amylolytic activity used for the invention can be both of purely microbial origin, purely animal origin or may also be a mixture of enzymes of animal and microbial origin.

In one variant of the invention, the enzyme mixture used is of purely microbial origin. Especially enzymes produced by bacteria, i. e. by the *Bacillus* or *Pseudomonas* strains, or by fungal cultures such as moulds, for example of the *Rhizopus* and *Aspergillus* strains, are especially suitable as microbial enzymes. Examples of such physiologically acceptable bacterial and/or mould fungi enzymes are already described in the state of the art, e. g. in connection with their synthesis and use for the treatment of maldigestion. Lipases may be derived from, for example, *Bacillus* or *Pseudomonas* strains, amylases and lipases from mould fungi, for example of the *Rhizopus* strain, and proteases, for example, also from Aspergillus.

Another preferred variant of the invention, however, involves the use of mixtures of digestive enzymes with lipolytic, proteolytic and amylolytic activity that in their properties closely resemble pancreatin. For the present invention, mixtures of digestive enzymes containing pancreatin and especially pancreatin itself are preferably used, and one or more microbial enzymes, i. e. enzymes synthesized by microorganisms, of the group of lipases, proteases and amylases may if desired be added to the pancreatin or the mixtures of digestive enzymes containing pancreatin.

Pancreatin is a known enzyme mixture with lipolytic, proteolytic and amylolytic activity which is available for example, under the trade name Creon®, in the form of granules, pellets or capsules containing enteric coated microspheres and is used medically for enzyme replacement, for example in pancreatic insufficiency, digestive insufficiency after stomach operations, liver and biliary diseases, cystic fibrosis and chronic pancreatitis. Pancreatin is generally obtained as a mixture of natural enzymes by extraction from porcine pancreas, for example according to the process described in German patent applications DE 25 12 746 and DE 42 03 315, and is then converted into the desired galenical form in a manner known in the art. The pancreatic enzymes are usually administered orally in the form of solid preparations.

In one variant of the invention, the pharmaceutical preparations manufactured and/or used in accordance with the invention contain preferably pancreatin or mixtures of digestive enzymes containing pancreatin. These pharmaceutical preparations manufactured according to the invention can contain pancreatin or mixtures of digestive enzymes containing pancreatin and if desired in addition to pancreatin one or more physiologically acceptable enzymes from the group of lipases, proteases and amylases, of the kind that can be obtained from microorganisms. Microbial enzymes suitable for use as this supplement include especially the bacterially synthesized enzymes already mentioned above, for example by the *Bacillus* or *Pseudomonas* strains, or by fungal cultures such as mould fungi, for example of the *Rhizopus* or *Aspergillus* strains. The lipases added to the pancreatin or the mixtures of enzymes containing pancreatin may originate, for example, from *Bacillus* or *Pseudomonas* strains, added amylases and lipases from mould fungi, for example of the *Rhizopus* strain, and added proteases, for example, also from *Aspergillus*.

It has now been found that the physiologically acceptable enzyme mixtures with lipolytic, proteolytic and amylolytic activity which can be obtained from microbial and/or animal sources and described with reference to this invention, can be used not only for the treatment of digestive enzyme deficiency states—of the kind associated for example with pathological changes of the pancreas due to chronic pancreatitis, digestive insufficiency after stomach operations, liver or biliary diseases—but surprisingly are also suitable for the treatment of primary diabetes mellitus in larger mammals and humans. In particular, the aforementioned physiologically acceptable enzyme mixtures with lipolytic, proteolytic and amylolytic activity, preferably however, for example, pancreatin itself or mixtures of digestive enzymes containing pancreatin which also contain microbial enzyme supplements, such as one or more microbial lipases, proteases and/or amylases, are suitable for adjuvant therapy in the management of diabetes, exert an additional effect supporting the diabetes therapy and beneficially influence the further course of the diabetic illness, i. e. especially by helping reduce the late complications of the diabetic disease.

The use of the physiologically acceptable enzyme mixtures, preferably, for example, pancreatin or mixtures of digestive enzymes containing pancreatin where appropriate with further microbial enzyme supplements in accordance with the invention also exhibits advantages in patients who in addition to the primary diabetes mellitus have complications relating to coexisting exocrine pancreatic insufficiency.

The pharmaceutical preparations manufactured and/or used according to the invention can contain in addition to the described microbial enzyme mixtures and/or mixtures of digestive enzymes of animal origin, such as especially pancreatin or mixtures of digestive enzymes containing pancreatin, pharmaceutical excipients and/or additives and, if appropriate, stabilizers.

For example, the enzyme mixtures may be contained in an effective quantity (in each case determined on the basis of the active units of the lipolytic, proteolytic and amylolytic components) together with conventional pharmaceutical excipients and/or vehicles in solid or liquid pharmaceutical preparations. The lipolytic activity per dose unit may be generally within a range of 5000 to 45000 Ph. Eur. lipase units, the proteolytic activity generally within a range of 200 to 3000 Ph. Eur. protease units and the amylolytic activity generally within a range of 3500 to 45000 Ph. Eur. amylase units (Ph. Eur.=European Pharmacopoeia). Examples of typical dose units are, for example, enzyme mixtures with the following activities: a) approx. 10000 Ph. Eur. lipase/ approx. 8000 Ph. Eur. amylase/approx. 600 Ph. Eur. protease; b) approx. 25000 Ph. Eur. lipase/approx. 18000 Ph. Eur. amylase/approx. 1000 Ph. Eur. protease; and c) approx. 40000 Ph. Eur. lipase/approx. 40000 Ph. Eur. amylase/ approx. 2600 Ph. Eur. protease units. Examples of solid formulations are preparations such as tablets, coated tablets, capsules, powder, granules or pellets for oral administration. These solid preparations may contain conventional inorganic and/or organic pharmaceutical vehicles such as lactose, talc or starch as well as conventional pharmaceutical excipients such as glidants or tablet disintegrants. Liquid preparations such as solutions, suspensions or emulsions of the active ingredients may contain the usual diluents such as water, oils and/or suspending agents such as polyethylene glycols and the like. Further excipients such as preservatives, flavouring agents, stabilizers (e. g. complex lipids) and the like may also be added.

The enzyme mixtures can be mixed and formulated with the pharmaceutical excipients and/or vehicles in a manner known to the art. To manufacture solid dosage forms, the enzyme mixtures may, for example, be mixed with the excipients and/or vehicles in the usual manner and wet or dry granulated or pelleted. Granules, pellets or powder can be filled directly into capsules or sachets or compressed into tablet cores in the usual manner. If desired, these cores can be coated to a dragee in the manner known to the art. Liquid preparations can be obtained by dissolving or dispersing the components and, if required, further excipients, in a suitable liquid vehicle, in the form of solutions or suspensions.

The antidiabetic effects and the beneficial influence on the course of the diabetic illness, especially in adjuvant therapy as part of an antidiabetic regimen, can be demonstrated for the physiologically acceptable enzyme mixtures with lipolytic, proteolytic and amylolytic activity used in accordance with the invention, such as, for example, the microbial enzyme mixtures and especially pancreatin or mixtures of digestive enzymes containing pancreatin described above, by determining the effect on pharmacological parameters of the kind generally used to evaluate diabetic diseases. Such parameters may, for example, be an improvement, i. e. decrease in glycosylated hemoglobin ($HbA_{1C}$), a decrease of blood glucose level, a reduced number of hypoglycaemic attacks and a decrease in hyperglycemia.

A double-blind, multi-center, placebo-controlled, parallel group study with pancreatin in the form of Creon® 10000 Minimicrospheres (minimicrospheres in capsules) was conducted in insulin-dependent diabetic patients (IDDM=type I) with coexisting exocrine pancreatic insufficiency to demonstrate the positive effects of the described enzyme mixtures on glycaemic control. The patient sample (male/female) was randomly assigned to groups each comprising 74 patients. Treatment was given over a period of four months at an oral dosage of 16 to 18 Creon capsules daily. Four capsules were administered with each of the main meals (3 daily) and two capsules with snacks (2 to 3 daily). One capsule of Creon® 10000 minimicrospheres contained 150 mg of pancreatin with the stated enzyme contents of 10000 Ph. Eur. lipase units, 8000 Ph. Eur. amylase units and 600 Ph. Eur. protease units. The placebo group received corresponding placebo minimicrosphere capsules without enzyme activities.

The efficacy of the enzyme mixture used in terms of the glycaemic control was determined by measuring the glycosylated hemoglobin level ($HbA_{1C}$). In this context a positive influencing of the $HbA_{1C}$ level as a clinically relevant improvement in the diabetes mellitus status is desired. Further diabetic parameters used were blood glucose levels (insulin/glucagon), evaluation of hypoglycaemic attacks, status of lipid soluble vitamins (A, D and E), daily insulin dose, body weight index and hyperglycaemic episodes.

Following a preliminary assessment for selection of the patient sample, the patients completed an initial start-up phase of 8 weeks (without administration of enzyme mixture/placebo) to establish the patients on individual insulin dosages. Before commencing the double-blind parallel groups study period of 4 months, a baseline assessment was carried out. The insulin dose was to remain as stable as possible during the study (±10%) with the exception of the first month of treatment in which an adjustment of the insulin dosage was allowed. Insulin adjustment required after randomization resulted in exclusion of the patient from the study, but short-term adjustments due, for example, to acute illness were allowed. The patients underwent two interim assessments in the first month of the study. Further assessments were carried out after six weeks of treatment and at the end of the study. Gastroenterologic parameters such as fecal fat, stool characteristics, coefficient of fat absorption (CFA) and clinical symptoms were evaluated separately from the diabetic parameters.

The above study showed that diabetic parameters are beneficially influenced by the administration of pancreatin, both in terms of a decrease of glycosylated hemoglobin ($HbA_{1C}$) as well as improved blood glucose control manifested, for example, by stabilization of blood glucose curves (smoothing) and, for example, reduction of the hypoglycaemic attacks and of hyperglycemia. The results of the study therefore demonstrate that the administration of physiologically acceptable enzyme mixtures with lipolytic, proteolytic and amylolytic activity according to the invention can bring about an improvement in diabetes mellitus status. It was demonstrated independently of these findings that in the group of diabetic patients with coexisting exocrine pancreatic insufficiency the gastroenterologic parameters such as fecal fat, stool characteristics, CFA and clinical symptoms are also beneficially influenced and that the overall nutritional status of these patients is improved. Physiologically acceptable enzyme mixtures with lipolytic, proteolytic and amylolytic activity—especially pancreatin or mixtures of enzymes containing pancreatin, also with the microbial enzyme supplements described—are therefore suitable for the manufacture of pharmaceutical preparations for the treatment of diabetes mellitus, especially for the adjuvant therapy of diabetes mellitus; in these cases the diabetes mellitus may also be accompanied by exocrine pancreatic insufficiency.

The pharmacological beneficial effects of the used enzyme mixture on the diabetic parameters and on the improvement of the diabetes mellitus status shall be further elucidated by the clinical study described in the following and by the results achieved therewith.

Clinical Study

For evaluating the efficiency of Creon® 10000 Minimicrospheres® in comparison to placebo on the glycaemic control of insulin dependent diabetic patients (IDDM=insulin dependent diabetes mellitus) with exocrine pancreas insufficiency a double-blind multicenter placebo-controlled parallel group study was conducted.

I. Study Design

The following clinical investigational report is an interim evaluation of a study on the efficacy of Creon® 10000 Minimicrospheres® in the treatment of insulin-dependent diabetic patients (IDDM) by glycaemic control. Thus, the report gives an overview on the study and on the interim results achieved after recruitment of about half of the required patients.

Study Objective

The main aim of this study was the evaluation of Creon® 10000 Minimicrospheres® on the glycemic control in insulin-dependent diabetic patients with pancreatic exocrine insufficiency.

Several variables are available to evaluate the glycemic control. The most important parameter is $HbA_{1C}$ which should be lower under the treatment group compared to the placebo group. This parameter was chosen as the main parameter. Additional parameters which were investigated include the number of hypoglycaemic attacks and hyperglycaemic episodes, fasting and postprandial blood glucose levels, daily insulin dose, body weight, plasma levels of fat-soluble vitamins (A/Dand E). Furthermore parameters of the exocrine dysfunction of the pancreas were assessed, including stool frequency and consistency, abdominal pain, meteorism, flatulence, clinical global impression of the disease rated by the patient and the investigator. Tolerability and safety were assessed by means of standard tests.

Patient Population

In this study patients with an insulin dependent diabetes mellitus were recruited. This patient population was chosen as a model sample for diabetes mellitus patients as this group is most clearly defined. It was planned to include 74 patients per treatment group leading to an overall sample size of 148 patients.

Patients should have had an onset of the disease before the age of 30 and should have started insulin therapy within the first year after diagnosis. Patients with proven non-insulin dependent diabetes mellitus were excluded.

To ensure that the patients being randomised had a certain degree of an pancreatic exocrine insufficiency the faecal elastase-1 values were evaluated. This parameter is a measure to determine the presence of an exocrine pancreatic dysfunction. To enter the study the value of elastase-1 had to be below or equal to 100 µg/g stool. Patients having values above were excluded from the study. Patients with an pancreatic exocrine insufficiency due to any other reasons than an insulin dependent diabetes mellitus (e.g. chronic pancreatitis, cystic fibrosis) also were excluded from the study.

Other inclusion criteria were: male and female gender and age of at least 18 years.

Further exclusion criteria were any other severe diseases which would have limited the participation in or completion of the study (exclusive of findings related to the underlying disease), known allergy to pancreatin and/or porcine insulin, any type of malignancy involving the digestive tract within the last five years, any type of gastrointestinal surgery and short bowel syndrome, haemachromatosis, any history of drug abuse including alcohol, positive urine pregnancy test or existing pregnancy or lactation (in females), severe allergy or any history of severe abnormal drug reactions, suspected non-compliance or non-cooperation, intake of any experimental drug within 4 weeks prior to the entry of the study and any other reason, in the investigator's opinion, that would prohibit the participation of the patient in the study.

Design:

All patients having signed the informed consent form underwent the pre-screening of elastase-1 in stools. If elastase-1 values were lower or equal to 100 µg/g stool and patients fulfilled the inclusion criteria and were not barred by exclusion criteria they could been entered into the run-in period of at least 8 weeks.

During the initial start-up period the patient should achieve a stable insulin dosage including no change in number of insulin injections and type of the insulin, no switch from standard treatment to intensive treatment or from injections to use of pumps. $HbA_{1C}$ levels should be in a range of 0.07 to 0.10 in metric units. Body weight had to be stable with not more than 5 kg difference between the assessments.

At the end of the initial start-up period suitable patients were randomised to either Creon® 10000 Minimicrospheres® or placebo. The treatment period was scheduled for 16 weeks with several interim assessments after 1, 2, 4 and 10 weeks and a final assessment at 16 weeks. During the first 4 weeks insulin adjustments were allowed. After 4, 10 and 16 weeks a wide range of investigations for glycaemic control were performed (see study objective).

Treatments and Dosages:

Patients were randomly allocated to Creon® 10000 Minimicrospheres® or to placebo. Patients were scheduled to receive 16 to 18 capsules/day. The number of capsules were fixed per meal. For the three main meals 4 capsules and for additional snacks (2 to 3) 2 capsules were taken by the patients.

This equals 40000 lipase Ph. Eur. units per main meal and 20000 lipase Ph. Eur. units per snack. A total daily dose of 160000 to 180000 lipase Ph. Eur. units was administered. This reflects the dose which has been used in clinical trials in chronic pancreatitis patients and should therefore be adequate for the treatment of patients with pancreatic exocrine insufficiency.

Statistics:

The analysis of the primary parameter was an analysis of covariance using a linear model with baseline as the covariate, the fixed main effects treatment and center, the measures followed over time, and the interaction of treatment by center. The alpha-level for the testing was 5%. The analysis was performed on the test group intended to be treated which consisted of all randomised patients having at least one $HbA_{1C}$ measurement under stable insulin dose after 4 weeks of treatment. As subsequently only the resulting interim analysis will be reported a peer-protocol sample has not been defined.

The sample size was calculated to be 74 patients per group using an alpha-level of 5%, a standard deviation for $HbA_{1C}$ of sigma=0.015 and a power of 80% to detect a difference of 0.007.

An interim analysis was planned as soon as half the patients completed the study (37 patients per group).

II. Results of the Clinical Study

Patient Group:

Due to low recruitment the interim analysis was performed with 71 patients being randomised to either Creon® 10000 Minimicrospheres® or placebo. The 71 patients were included in the safety sample and received at least one dose of study drug.

Based on the criteria for the test group intended to be treated (intent-to treat sample,=ITT) 65 patients could be used for the analysis of $HbA_{1C}$ (Table 1).

TABLE 1

Patient Test Group

|  | Placebo N | Creon N | Total N |
|---|---|---|---|
| Safety sample | 36 | 35 | 71 |
| ITT sample | 36 | 29 | 65 |

ITT = intent-to treat

Demographic Data:

The following Table 2 gives an overview on the most important demographic data.

TABLE 2

Demographic Data

| Parameter | Placebo | Creon | Total |
|---|---|---|---|
| Sex [N(%)] | | | |
| Male | 21 (58.3) | 23 (65.7) | 44 (62.0) |
| Female | 15 (41.7) | 12 (34.3) | 37 (38.0) |
| Ethnic origin [N(%)] | | | |
| Caucasian | 36 (100.0) | 34 (97.1) | 70 (98.6) |
| Black | — | 1 (2.9) | 1 (1.4) |
| Age [years] | | | |
| Mean ± SD | 42.7 ± 10.0 | 46.6 ± 8.9 | 44.6 ± 9.6 |
| Range | 24–64 | 30–63 | 24–64 |
| male (mean ± SD) | 44.7 ± 10.4 | 45.7 ± 9.7 | 45.2 ± 10.0 |
| female (mean ± SD) | 40.0 ± 9.0 | 48.3 ± 7.3 | 43.7 ± 9.2 |
| Weight [kg] | | | |
| Mean ± SD | 74.5 ± 11.8 | 79.2 ± 12.9 | 76.8 ± 12.5 |
| Range | 47–93 | 54–103 | 47–103 |
| Male (mean ± SD) | 79.8 ± 9.0 | 84.7 ± 9.3 | 82.4 ± 9.4 |
| Female (mean ± SD) | 67.0 ± 11.5 | 68.6 ± 12.5 | 67.7 ± 11.8 |
| Height [cm] | | | |
| Mean ± SD | 171.1 ± 10.1 | 173.2 ± 10.0 | 172.1 ± 10.0 |
| Range | 152–190 | 156–191 | 152–191 |
| Male (mean ± SD) | 176.3 ± 7.4 | 179.1 ± 6.4 | 177.8 ± 7.0 |
| Female (mean ± SD) | 163.8 ± 8.7 | 161.8 ± 3.6 | 162.9 ± 6.9 |
| BMI [kg/m$^2$] | | | |
| Mean ± SD | 25.4 ± 3.0 | 26.4 ± 3.6 | 25.9 ± 3.3 |
| Range | 18–31 | 19–34 | 18–34 |
| Male (mean ± SD) | 25.7 ± 2.6 | 26.5 ± 3.2 | 26.1 ± 3.0 |
| Female (mean ± SD) | 24.9 ± 3.6 | 26.1 ± 4.3 | 25.5 ± 3.9 |

SD = Standard Deviation
BMI = Body Mass Index

As can be seen from the table, both treatment groups were comparable concerning demographic data, although some more males were randomised in the Creon group which subsequently led to slightly higher values for height, weight and BMI in the Creon group. However, these differences can be regarded as not being important for the interpretation of the efficacy results.

The same is true for the age of onset of diabetes, duration of the disease or duration of insulin treatment. In all cases there are only small differences in the mean or median values between the two treatment groups. Therefore, the disease severity can be regarded as similar in both treatment arms.

The elastase-1 values at pre-screening were also not significantly different between the two groups (57.3±26.5 for Creon versus 62.0±29.8 for placebo).

Efficacy Parameter:

The results of the most important parameter the $HbA_1$, are summarised in Table 3. The table contains the data from the ITT sample.

TABLE 3

$HbA_{1c}$ - ITT sample

|  | Placebo | | Creon | |
|---|---|---|---|---|
|  | N | mean | N | mean |
| Week 4 | 36 | 0.07967 | 29 | 0.07779 |
| Difference between treatments | Mean: 0.00187 SEM: 0.00086 | | | |
|  | P = 0.0330 | | | |

TABLE 3-continued

HbA$_{1c}$ - ITT sample

|  | Placebo | | Creon | |
| --- | --- | --- | --- | --- |
|  | N | mean | N | mean |
| Week 10 | 36 | 0.08131 | 29 | 0.07876 |
| Difference between treatments | Mean: 0.00254 SEM: 0.00112 P = 0.0268 | | | |
| Week 16 | 36 | 0.08273 | 29 | 0.08034 |
| Difference between treatments | Mean: 0.00238 SEM: 0.00138 P = 0.0902 | | | |

SEM = Standard Error of the Mean

Table 3 shows that Creon leads to statistically significant lower levels of HbA$_{1c}$ after 4 and 10 weeks and a clear trend even after 16 weeks. This indicates that Creon has the potential to improve glycaemic control in patients with insulin-dependent diabetes mellitus.

This is underscored by Table 4 showing the number of patients being improved, unchanged or worsened compared to baseline HbA$_{1c}$ values.

TABLE 4

Number of patients improved, unchanged or worsened compared to baseline concerning HbA$_{1c}$

|  | Placebo | | | Creon | | |
| --- | --- | --- | --- | --- | --- | --- |
|  | improved | unchanged | worsened | improved | unchanged | worsened |
| Week 4 | 13 | 5 | 18 | 15 | 5 | 9 |
| Week 10 | 12 | 2 | 22 | 12 | 5 | 12 |
| Week 16 | 4 | 4 | 26 | 11 | 3 | 15 |

Many more patients under placebo treatment had a worsening of their HbA$_{1c}$ levels over time compared to the Creon-treated group. The tendency to worsen was relatively small under Creon treatment, whereas under placebo the majority of patients got worse. This is again a clear indication that Creon is effectively able to improve the glycaemic control of insulin-dependent diabetes mellitus. The reason why many patients worsened is based on the study design which requires a nearly optimal treatment before randomisation which leads under normal condition to a rapid deterioration of the glycaemic control as seen by the placebo group. The test show that Creon is able to reduce this deterioration.

Similar findings were observed for the occurrence of the number of mild to moderate hypoglycaemic attacks (Table 5).

TABLE 5

Change of number of hypoglycaemic attacks

|  | Placebo | | | Creon | | |
| --- | --- | --- | --- | --- | --- | --- |
|  | <0 | =0 | >0 | <0 | =0 | >0 |
| Week 4 | 11 | 9 | 16 | 8 | 7 | 14 |
| Week 10 | 13 | 13 | 10 | 13 | 3 | 11 |
| Week 16 | 14 | 10 | 12 | 14 | 8 | 8 |

<0 less number of attacks compared to baseline
=0 same number of attacks compared to baseline
>0 greater number of attacks compared to baseline Table 5 shows that nearly 50% of the patients receiving Creon had fewer mild and moderate hypoglycaemic attacks compared to the placebo group where only 39% had this finding.

For the number of increased glucose levels per week—an indicator of hyperglycaemic periods—a similar but slightly weaker effect was found.

Fasting and non-fasting blood glucose levels were not significantly different as well as the dosage of insulin needed by the patients.

The number of adverse events was not different between the two treatment arms. Some more adverse events were observed in the digestive system under Creon treatment and more adverse events in the metabolic/nutritional disorder and respiratory system group of adverse events were noted under placebo treatment. The number of patients dropping out for adverse events were the same in both groups.

III. Conclusion

Overall, there is strong evidence that Creon is beneficial in the treatment of insulin-dependent diabetic patients having exocrine pancreatic insufficiency and leading to a better glycaemic control. This means that Creon should be added to the treatment of those patients in order to improve the most important factor in their treatment.

As insulin-dependent diabetic patients have been used a model it can be estimated that the same beneficial effects will be seen in non-insulin-dependent diabetic patients as long as they would have a pancreatic exocrine insufficiency as well.

The following example illustrates the manufacture of a pharmaceutical preparation containing pancreatin which is suitable for the treatment of diabetes, and especially for adjuvant therapy of diabetes, without, however, restricting the scope of the invention.

EXAMPLE 120 kg of pancreatin were mixed in a conventional mixer with 30 kg of polyethylene glycol 4000 and thoroughly moistened with about 20 kg of propan-2-ol. The mixture was pressed through an extruder fitted with a perforated plate with holes of 0.8 mm internal diameter and a downstream cutting device. This arrangement produced strands of extruded material with a length of up to 20 mm. The strand sections were crushed in portions of about 15 kg in a rounding machine (type Caleva) and rounded into spherically shaped pellets, whereby 300 g of liquid paraffin and, depending on the time spent by the material in the rounding machine (3 to 6 min), about 300 to 700 g of propan-2-ol was added to each portion. After drying in a conventional tray drier, a yield of about 90% of pancreatin microsphere cores with a diameter of 0.7 to 1.4 mm, screened through a 0.7 mm sieve (separation of undersized particles<0.7 mm) and a 1.4 mm sieve (separation of oversized particles>1.4 mm), with a pancreatin content of about 78% was obtained. The bulk density was 0.7 g/ml. The microsphere cores were then provided with an enteric coating in the manner known to the art in a conventional film coating apparatus, using a solution of hydroxypro-pylmethyl-cellulose phthalate (type HP55), dibutyl phthalate, liquid paraffin and silicon oil (Dimethicone 1000) in acetone. The resulting yield was about 90% enteric-coated pancreatin microspheres with a diameter ranging between 0.7 to 1.6 mm, screened with a 0.7 mm sieve (separation of undersized particles<0.7 mm) and a 1.6 mm sieve (separation of oversized particles>1.6 mm) with a content of about 60% pancreatin, with reference to the film-coated microspheres, and a bulk density of 0.8 g/ml. The microspheres were then filled into conventional hard gelatin capsules or sachets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method of treating a larger mammal or human suffering from primary diabetes mellitus Type I comprising administering to said mammal or human an effective amount of a pharmaceutical preparation comprising a physiologically acceptable enzyme mixture having lipolytic, proteolytic and amylolytic activity.

2. A method according to claim 1, wherein said pharmaceutical preparation comprises a physiologically acceptable enzyme mixture of microbially synthesized lipases, proteases and amylases.

3. A method according to claim 1, wherein said pharmaceutical preparation comprises pancreatin.

4. A method according to claim 1, wherein said pharmaceutical preparation comprises a mixture of digestive enzymes containing pancreatin.

5. A method according to claim 3, wherein said pharmaceutical preparation comprises pancreatin or a mixture of digestive enzymes containing pancreatin, and at least one microbial enzyme selected from the group consisting of lipases, proteases and amylases.

6. A method according to claim 1, wherein said pharmaceutical preparation is administered as an adjuvant therapy in conjunction with another, primary therapy.

7. A method according to claim 1, wherein said larger mammal or human is a patient suffering from diabetes mellitus accompanied by exocrine pancreatic insufficiency.

* * * * *